United States Patent
Tapas Kumar et al.

(10) Patent No.: US 7,402,706 B2
(45) Date of Patent: Jul. 22, 2008

(54) POLYISOPRENYLATED BENZOPHENONES AND THEIR ISOMERS AS INHIBITORS OF HISTONE ACETYLTRANSFERASES AND USES THEREOF

(75) Inventors: Kundu Tapas Kumar, Bangalore (IN); Karanam Balasubramanyam, Bangalore (IN); Kempegowda Mantelingu, Mysore District (IN); Altaf Mohammad, Jammu and Kashmir (IN); Venkatesh Swaminathan, Kolkata (IN); A. Varier Radhika, Coimbatore (IN)

(73) Assignee: Jawaharlal Nehru Centre for Advanced Scientific Research, Bangalore (IN)

( * ) Notice: Subject to any disclaimer, the term of this patent is extended or adjusted under 35 U.S.C. 154(b) by 0 days.

(21) Appl. No.: 10/579,219

(22) PCT Filed: Nov. 4, 2004

(86) PCT No.: PCT/IB2004/052294

§ 371 (c)(1),
(2), (4) Date: Mar. 9, 2007

(87) PCT Pub. No.: WO2005/047457

PCT Pub. Date: May 26, 2005

(65) Prior Publication Data

US 2007/0254961 A1    Nov. 1, 2007

(30) Foreign Application Priority Data

Nov. 13, 2003    (IN) .................................. 929/03

(51) Int. Cl.
C07C 49/00    (2006.01)
A61K 31/12    (2006.01)

(52) U.S. Cl. ........................................ 568/325; 514/685

(58) Field of Classification Search ........................ None
See application file for complete search history.

(56) References Cited

OTHER PUBLICATIONS

Fuller et al. Guttiferone F, the first Prenylated Benzophenone from *Allanblackia stuhlmannii*. Journal of Natural Products, 1999, vol. 62, pp. 130-132.*
Roux et al. Structure- Activity Relationship of Polyisoprenyl Benzophenones from *Garcinia pyrifera* on the Tubulin-Microtuble System. Journal of Natural Products, 2000, vol. 63, pp. 1070-1076.*
Rao et al. Camboginol and Cambogin. Tetrahedron Letters, 1980, vol. 21 (20), pp. 1975-1978.*
Krishnamurthy et al. Crystal and Molecular Structure of Isogarcinol. Tetrahedron Letters, 1982, vol. 23 (21), pp. 2233-2236.*

* cited by examiner

*Primary Examiner*—Sikarl A Witherspoon
(74) *Attorney, Agent, or Firm*—Hamre, Schumann, Mueller & Larson, P.C.

(57)    ABSTRACT

In this patent we describe the purification of prenylated benzophenones from the fruit rinds of *Garcinia* species and its evaluation as an inhibitor for Histone acetyltransferases p300 and PCAF. We have found that prenylated benzophenones are potent HAT inhibitors of p300 ($IC_{50}$-1 μM) and pCAF ($IC_{50}$-15 μM). The inhibitors significantly repress the p300 HAT dependent transcriptional activation from in vitro assembled chromatin template but had no effect on transcription from DNA. These results suggest that the compounds could be specific to HATs. Thus these compounds should be useful as biological switching molecule for evaluating the role of p300 and PCAF in cellular functions and may be useful as new chemical entities for the development of anticancer drugs.

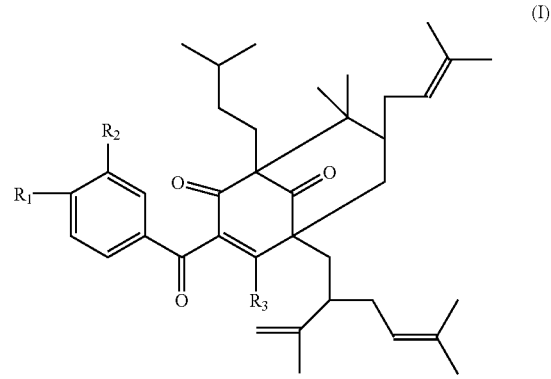

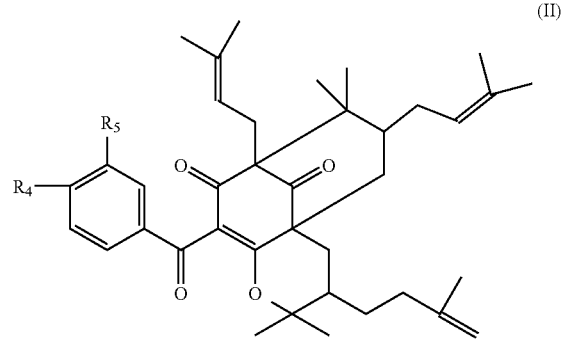

10 Claims, 2 Drawing Sheets

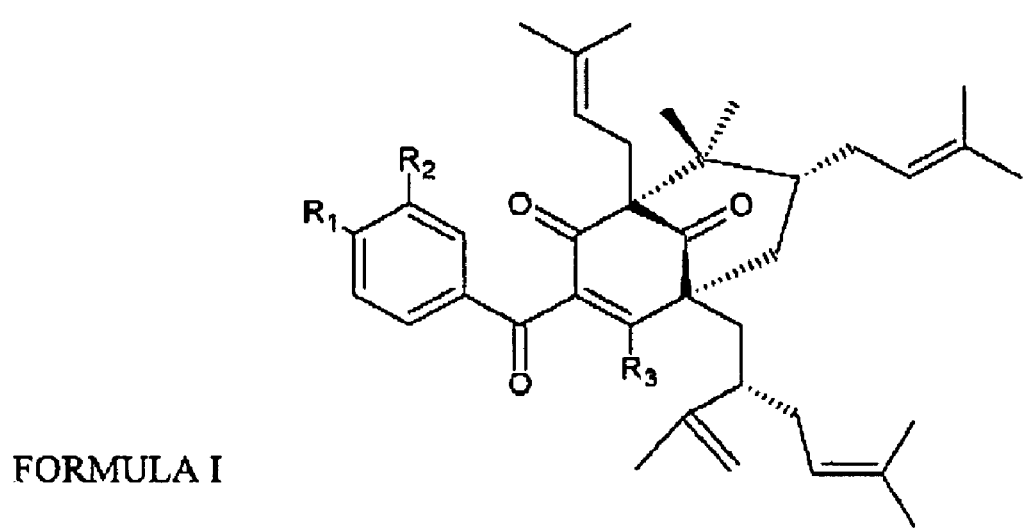
FORMULA I
FIG. 1.0

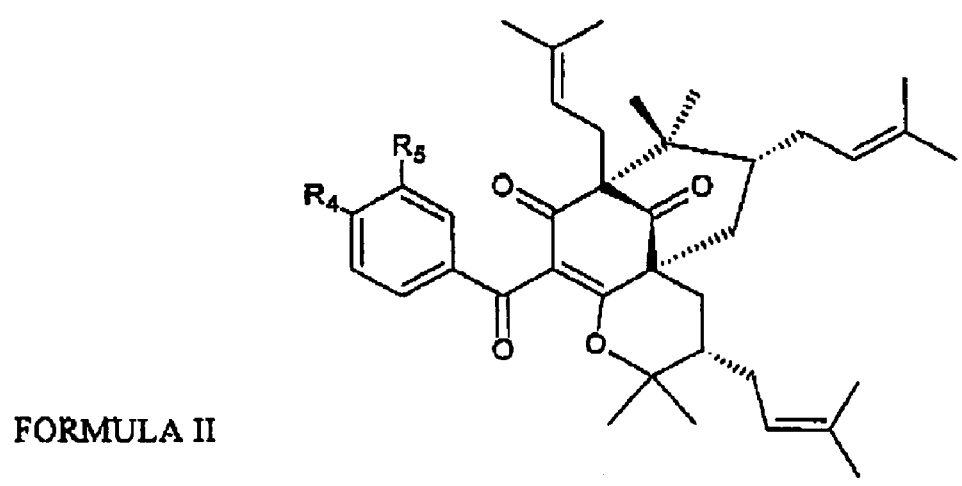
FORMULA II
FIG. 2.0

POLYISOPRENYLATED BENZOPHENONES AND THEIR ISOMERS AS INHIBITORS OF HISTONE ACETYLTRANSFERASES AND USES THEREOF

FIELD OF INVENTION

This invention relates to the field of novel anticancer therapeutics, which can also be used for treating several other diseases (HIV, cardiac hypertrophy, asthma) in humans.

PRIOR ART

The acetylation and deacetylation of histones plays a key role in the regulation of gene expression in eukaryotic cells (1). The acetylation status of histones alters chromatin structure, and thereby modulates gene expression. Two classes of enzymes can effect the acetylation of histones, histone acetyltransferases (HATs) and histone deacetylases (HDACs) (1, 2). Interestingly, these enzymes can also acetylate or deacetylate several non-histone substrates with functional consequences (1, 3). Altered HAT and HDAC activities can lead to several diseases, ranging from cancer to neurodegenerative diseases (4, 5, 6, 7).

Several families of HATs have recently been identified, which includes, GNAT family (GCN 5-related N-acetyltransferase), the MYST group, SAS2, TIP60, and p300/CBP families (1, 3). The p300/CBP family of HAT is represented by two of the most widely studied HATs, p300 and CBP. These proteins share considerable sequence and functional homology. Several lines of evidence indicate that p300/CBP are involved in cell cycle progression and cellular differentiation (8, 9, 10, 11). Mechanistically, these proteins function as transcriptional coactivators through their direct interaction with a diverse group of transcription factors and the RNA polymerase II transcription machinery. The coactivation function is partially facilitated by their intrinsic HAT activity (12, 13). Mutations in the HAT active site abolishes their transactivating function (1). The p300/CBP associated factor, PCAF is one of the important HATs of the GNAT family. The C-terminal half of PCAF has a very significant sequence similarity to yeast GCN5 (14). In humans there are two GCN5 splice variants, hGCN5 and hGCN5-L (long form) synthesized from the same gene. The hGCN5-L is similar in length to PCAF and shares 75% amino acid sequence identity with PCAF. It also interacts with p300/CBP. The hGCN5-L is thus termed as PCAF-B (15). PCAF-B is an essential gene expressed ubiquitously early in development, whereas PCAF is expressed later in embryonic development and is not essential (16). In vivo PCAF exists in a large multi-protein complex, containing more than 20 different polypeptides (17). Unlike p300/CBP (which acetylates all the four core histones, predominantly H3 and H4) PCAF acetylates predominantly histone H3. For nucleosomal histone substrates, this specificity is quite exclusive. The acetylase domain of PCAF is required for MyoD-dependent coactivation and differentiation. Presumably the acetyltransferase activity of PCAF and PCAF-B is also involved in DNA repair (15). Both p300/CBP and PCAF also target non-histone protein substrates, which include, human transcriptional coactivators, PC4 (18), HMGB-1 (19), HMG17, HMGI/Y; transcription factors E2F, p53, GATAL (3), and HIV Tat protein (20, 21). The acetylation of these factors alter their DNA/nucleosome binding and/or protein-protein interactions and consequently influence their effect in regulating gene transcription.

It is thus evident that proper balance of acetylation and deacetylation is important for normal cell proliferation, growth and differentiation. The dysfunction of these machineries leads to different diseases. Several lines of evidence indicate that HAT activity is associated with tumor suppression and the loss or misregulation of this activity may lead to cancer. For example, viral oncogene proteins E1A target p300/CBP, disrupting its interaction with PCAF (14). E1A interaction with p300/CBP is essential for cellular transformation. Chromosomal translocations associated with certain leukemias indicate that gain of function mutations in CBP is also oncogenic (22). Mutations in HATs cause several other disorders other than cancer. Mutations in CBP result(s) in the Rubinsten-Taybi syndrome (RTS) (23). It was found that a single mutation at the PHD domain of CBP causes this syndrome. Interestingly, this mutation (G to C at 4951) in CBP also abolishes its HAT activity (23, 24). Degradation of CBP/p300 was found to be associated with certain neurodegenerative diseases (7). Proper HAT function is also essential for the replication of HIV. It was elegantly shown that treatment with HDAC inhibitors inhibits the latency of HIV, presumably by inducing acetylation of Tat protein and the nucleosomes on the LTR (25, 26). These examples clearly indicate that histone acetyltransferases and deacetylases should be one of the potential targets for therapy. During the last decade, a number of HDAC inhibitors have been identified that induce apoptosis in cultured tumor cells (4). These inhibitors were also found to be potent anticancer agents in vivo. Furthermore, some of these inhibitors (e.g. SAHA) are already in human trial as antineoplastic drug (27). Although substantial progress has been made in the study of HDAC inhibitors, very little is known about HAT inhibitors. Initially, before the discovery of HATs, polyamine-CoA conjugates were found to inhibit the acetyltransferase activity of cell extracts (28). Availability of recombinant HATs (p300 and PCAF) made it possible to synthesize more targeted specific inhibitors, Lys-CoA for p300 and H3-CoA-20 for PCAF (29). However, these inhibitors could not permeate the cells and were found to be pharmacogenically poor (30). Recently, we have discovered a natural inhibitor anacardic acid from cashew nut shell liquid that potently inhibits both p300 and PCAF (31). Based on anacardic acid we have synthesized a small molecule activator of p300, CTPB. Interestingly, CTPB is specific for p300. Both anacardic acid and CTPB may serve as a potential lead compounds for designing different drugs.

SUMMARY OF INVENTION

We report that garcinol, a polyisoprenylated benzophenone derivative from *Garcinia indica* fruit rind, is a potent inhibitor of histone acetyltransferases p300 ($IC_{50} \approx 7$ µM) and PCAF ($IC_{50} \approx 5$ µM) both in vitro and in vivo. The kinetic analysis shows that it is a mixed type of inhibitor with an increased affinity for PCAF as compared to p300. HAT activity dependent chromatin transcription was strongly inhibited by garcinol, whereas transcription from DNA template was not affected. Furthermore, it was found to be a potent inducer of apoptosis, and it alters (predominantly down regulates) the global gene expression in HeLa cells. Further derivatives have been obtained from the basic compound by known methods and tested for efficacy as Histone acetyl transferase inhibitors and all compounds have an $IC_{50}$ concentration ranging from 5 to 7 µM. The compounds have potential for use as anticancer drugs, Based on known prior art for Histone acetyl transferase inhibitors, the compounds can also be used for treating several other diseases (HIV, cardiac hypertrophy, asthma) in humans.

DESCRIPTION OF THE INVENTION

EXAMPLE 1.0

Purification and Structural Analysis of Garcinol

Garcinol was prepared from *Garcinia indica* fruit rind (46). In brief, *G. indica* dried fruit (Kokum) rind was extracted with ethanol, and the extract was fractionated by ODS (octadecyl silica) column chromatography eluted stepwise with 60-80% aqueous ethanol. The fractions containing garcinol were concentrated and dried in vacuum. The residue was dissolved in hexane, and the solution was cooled at 5° C. for 2 days. Yellow amorphous precipitate was collected from the solution and washed with cold hexane and recrystallized at room temperature. Pale yellow needle crystals were obtained from the solvent, which were identified as garcinol from the following spectral data: mp 126° C.; Optical rotation at 30-135 ($CHCl_3$); UV in EtOH (log $\epsilon$) 367 (3.84) and 250 (4.05) nm; IR 3200-3500, 1730, 1640 $cm^{-1}$; $^1H$ NMR ($CDCl_3$) δ 6.95 (1H, dd, J=9.0 and 2.0 Hz), 6.91 (1H, d, J=2.0 Hz), 6.60 (1H, d, J=9.0 Hz), 4.96, 5.06, 5.10 (1H each, t, J=5.0 Hz), 4.40 (d, J=15.0 Hz), 2.80-1.46 (m, 12H, methylene and methyne), 1.78, 1.74, 1.69, 1.62, 1.59, 1.56, 1.21, 1.05 (3H each, s); EI-MS m/z 602 $[M]^+$, 533, 465, 341.

IUPAC name: 3-(3,4-Dihydroxy-benzoyl)-4-hydroxy-5-(2-isopropenyl-4-methyl-pent-3-enyl)-8,8-dimethyl-1-(3-methyl-but-2-enyl)-7-(4-methyl-pent-3-enyl)-bicyclo[3.3.1]non-3-ene-2,9-dione

BRIEF DESCRIPTION OF THE DRAWINGS

FIG. 1.0 depicts a Garcinol derivative according to the present invention.

FIG. 2.0 depicts an Isogarcinol derivative according to the present invention.

EXAMPLE 2.0

Histone Acetyl Transferase (HAT) Assay

The protocol used for the HAT assays is described elsewhere (32). Indicated amounts of proteins (see the Figure legends) were incubated in HAT assay buffer containing 50 mM Tris-HCl, pH 8.0, 10% (v/v) glycerol, 1 mM dithiothreitol, 1 mM phenylmethylsulphonyl fluoride (PMSF), 0.1 mM EDTA pH 8.0, 10 mM sodium butyrate at 30° C. for 10 min in the presence and absence of garcinol followed by addition of 1 μl of 4.7 Ci/mmol [$^3H$]-acetyl CoA and were further incubated for another 10 min. The final reaction volume was 30 μl. The reaction mixture was then blotted onto P-81 (Whatman) filter paper and radioactive counts were recorded on a Wallace 1409 liquid scintillation counter. To visualize radiolabeled acetylated histones, the reaction products were resolved on 15% SDS-polyacrylamide gel and subjected to fluorography followed by autoradiography as described earlier (32) For the kinetic analysis of garcinol-mediated inhibition of HATs, filter binding assay was performed by known methods.

EXAMPLE 3.0

Histone Deacetylase Assay

Deacetylation assay was performed as described previously (31), Briefly 2.4 μg of core histones were incubated in HAT buffer without NaBu, with 20 ng of p300 and 1 μl of 4.7 Ci/mmol [$^3H$]-acetyl CoA for 30 min at 30° C. The activity of p300 was inhibited by incubating the reaction mixture with 10 nM p300 specific inhibitor Lysyl-CoA (29) for 15 min at 30° C., after which 50 ng of baculovirus expressed and purified recombinant histone deacetylase HDAC1 was added in the presence or absence of garcinol and incubated further for 45 min at 30° C. The samples were analysed as described above.

EXAMPLE 4.0

Analysis of in Vivo Acetylated Histones by Acid/Urea/Triton(Aut) Polyacrylamide Gel Electrophoresis HeLa cells ($3\times10^6$ cells per 90 mm dish) were seeded overnight and histones were extracted from the cells after 24 hours of compound treatment as described elsewhere (34). Briefly, cells were harvested, washed in ice-cold buffer A (150 mM KCl, 20 mM Hepes, pH 7.9, 0.1 mM EDTA and 2.5 mM $MgCl_2$) and lysed in buffer A containing 250 mM sucrose and 1% (v/v) Triton X 100. Nuclei were recovered by centrifugation, washed, and proteins were extracted for 1 h using 0.25 M HCl. Chromosomal proteins were precipitated with 25% (w/v) trichloroacetic acid (TCA) and sequentially washed with ice cold acidified acetone (20 μl of 12N HCl in 100 ml acetone), and acetone, air-dried and dissolved in the sample buffer (5.8 M urea, 0.9 M glacial acetic acid, 16% glycerol, and 4.8% 2-mercaptoethanol). The protein was quantitated using a protein assay reagent. (Biorad). The histones were resolved on AUT gel as described elsewhere (35, 36). Briefly, 8 cm of the separating gel (1 M acetic acid, 8 M urea, 0.5% Triton X-100, 45 mM NH3, 18% acrylamide mix and 0.5% TEMED) was overlaid with 2 cm of an upper gel (1 M acetic acid, 8 M urea, 0.5% Triton X-100, 45 mM NH3, 3.3% acrylamide, 0.16% bisacrylamide and 0.5% TEMED) and polymerization was aided with 0.0003% riboflavin. The gel was pre-electrophoresed for 3-4 hours at 130V in running buffer (1M acetic acid) until the current no longer dropped. Fresh running buffer was added prior to loading the samples (0.2% methyl green was added as the tracking dye) and the gel was run overnight at 130V and subsequently stained with Coomassie brilliant blue.

EXAMPLE 5.0

In Vitro Chromatin Assembly

Chromatin template for in vitro transcription experiments was assembled and characterized as described earlier (12).

EXAMPLE 6.0

In Vitro Transcription Assay

Transcription assays were essentially carried out as described previously (12) with some modifications. Briefly, the reconstituted chromatin template (containing 30 ng DNA) or an equimolar amount of histone-free DNA was incubated with 50 ng of activator (Gal4-VP16) in a buffer containing 4 mM HEPES (pH 7.8), 20 mM KCl, 2 mM DTT, 0.2 mM PMSF, 10 mM sodium butyrate, 0.1 mg/ml bovine serum albumin, 2% glycerol. p300 was preincubated with indicated amounts of garcinol at 20° C. for 20 min following which it was added to the transcription reaction and incubated for 30 min at 30° C. After acetylation, HeLa nuclear extract (5 μl, which contains 8 mg/ml protein) was added to initiate the preinitiation complex formation. Transcription reaction was started by the addition of NTP-mix and α-[$^{32}$P] UTP after the preinitiation complex formation. The incubation was continued for 40 min at 30° C. A separate reaction was setup with ~25 ng of supercoiled ML200 DNA, and the transcription assay was carried out as described above, without the addition of the activator (Gal4-VP16). 2 μl of this reaction was added to each of the transcription reactions to serve as a loading control. The transcription reactions were terminated by the addition of 250 μl of stop buffer (20 mM Tris-HCl pH 8.0, 1 mM EDTA, 100 mM NaCl, 1% SDS and 0.025 ng/μl tRNA). Transcripts were analysed by 5% Urea-PAGE and visualized by autoradiography. Quantification of transcription was done by phosphoimager (Fuji) analysis.

EXAMPLE 7.0

Apoptosis Assay

Garcinol induced apoptosis was monitored by the extent of chromatin fragmentation. DNA was extracted from the untreated and garcinol-treated HeLa cells. The cells (3×10$^6$ per 90 mm dish) were seeded and treated with the compound for 24 hours. Harvested cells were washed with PBS and then lysed with lysis buffer containing 0.5% Triton X-100, 20 mM Tris and 15 mM EDTA at room temperature for 15 minutes. The lysate was treated with RNase (0.1 mg/ml) and Proteinase K (2 mg/ml) for 1 h, extracted with phenol/chloroform/isoamyl alcohol (25:24:1) and DNA was precipitated by incubating the upper aqueous phase with 0.1 volumes of 3 M sodium acetate (pH 5.2) and 1 volume of isopropanol overnight at −20° C. The pellet obtained on centrifugation washed with 70% ethanol and dissolved after air-drying in 50 μl of TE buffer. The extracted DNA was analyzed on a 1.8% agarose gel and visualized by ethidium bromide staining. Nuclei fragmentation was also visualized by hoechst staining of apoptotic nuclei. The apoptotic cells were collected by centrifugation, washed with PBS and fixed in 4% paraformaldehyde for 20 minutes at room temperature. Subsequently the cells were washed and resuspended in 20 μl PBS before depositing it on polylysine-coated coverslips. The cells were left to adhere on cover slips for 30 min at room temperature after which the cover slips were washed twice with PBS. The adhered cells were then incubated with 0.1% Triton X-100 for 5 min at room temperature and rinsed with PBS for three times. The coverslips were treated with Hoechst 33258 for 30 minutes at 37° C., rinsed with PBS and mounted them on slides with glycerol-PBS. Stained nuclei were analysed by using Axioskop-2-plus upright microscope with epi-fluorescence equipment (Carl Zeiss) and the image was captured by Axiocam MRC camera and analyzed by AxioVision 3.1 software.

EXAMPLE 8.0

Microarray Analysis

The microarrays used in this study were procured from the Microarray centre, University Health Network, Toronto, Ontario. Each array carries 19200 spots from the human genome, arranged in 48 individual arrays of 400 spots each. Each of the 48 grids contains 3 Arabidopsis spots that serve as local controls. The total RNA was isolated from control and treated cells using RNaeasy kit (Sigma catalog #74103). The micromax indirect labeling kit (Perkin Elmer Life Science catalog #MPS521) was used to synthesize the labeled cDNA from 4 μg of total RNA and further process the hybridized cDNA on the array by the tyramide signal amplification method (37). All the steps were carried out according to the manufacturer's recommendations (http://www.nen.com/pdf/penen264-mmaxaminated_card.pdf). The array slides were scanned immediately using a GenePix Presonal 4100A Axon Scanner. The images were analysed using the GenePix software and the Genowizard software (Genotypic Technology, Bangalore) was used for grid wise normalization of the array. Six arrays were used with two biological repeats of the treatment of cells and at least two dye swap experiments were included in the final analysis. The genes that were picked up as differentially regulated had a log mean of at least 1.27489 with S.D less than 20% of the expression change in the case of up-regulated genes and a log mean of almost −1.75726 with S.D less than 37% of the expression change in case of the down-regulated genes. Guidelines set by MIAME were followed and the raw microarray data will be deposited in the GEO database (http://www.ncbi.nlm.nih.gov/geo/).

RESULTS

The HAT inhibitory activity was assayed using baculovirus-expressed recombinant histone acetyltransferases p300 and PCAF and highly purified HeLa core histones as substrate. Garcinol was found to be a highly efficient inhibitor of PCAF acetyltransferase activity (Inhibition of the histone acetyltransferase activity of PCAF was assayed similar to the HAT assay performed for determination of p300 HAT activity) with IC$_{50}$ of approximately 5 μM under similar conditions the IC$_{50}$ of the inhibitor for p300 acetyltransferase activity was approximately 7 μM. These results suggest that although garcinol inhibits the HAT activity of both p300 and PCAF, it is relatively more potent as well as a faster inhibitor of PCAF as compared to p300. In order to further confirm these results we analyzed the HAT assay products on SDS-PAGE followed by fluorography. In agreement with the results of the p300 filter binding assay, it was found that the HAT activity of PCAF was almost completely inhibited by 10 μM of garcinol as compared to DMSO control, whereas even at 20 μM concentration 5-10% of [$^3$H]-labelled histone H3 could be detected that acetylation of histone H4 by p300 was more sensitive to inhibition by garcinol as compared to that of H3. The p300 mediated acetylation of histone H4 was completely inhibited at 1 μM concentration of garcinol, while 20 μM of it could not abolish the acetylation of H3. After establishing garcinol as a strong inhibitor of HATs in vitro, we further investigated whether it could also affect the acetylation of histones in vivo. For this purpose HeLa cells were grown in monolayer (see experimental procedures) and were treated with either DMSO (the solvent for garcinol) or different concentrations of garcinol, and histones were extracted from the cell pellet and analyzed on an 18% acid/urea/triton polyacrylamide gel electrophoresis. As seen from the profile of different histones, incubation with the compound alone did not alter the acetylation status of the cellular histones significantly. In agreement with the previous reports (38) the bulk histones from HeLa cells are found to be largely unacetylated. Since the global acetylation of histones for asynchronous cells does not change significantly, it was not possible to find out the effect of HAT inhibitor on histone acetylation. In order to stimulate histone acetylation, cells were treated with deacetylase inhibitors TSA and sodium butyrate. As expected deacetylase inhibitors enhance the acetylation of histone H4 as well as H2B dramatically. The treatment of the cells with garcinol along with TSA and sodium butyrate significantly inhibits the enhanced acetylation of H4 as well as H2B. Taken together, these results establish that garcinol is a potent inhibitor of histone acetyltransferases in vitro and in vivo.

In order to understand the nature of inhibition as well as of the mechanism of inhibition brought about by garcinol we analysed the kinetics of inhibition for both p300 and PCAF.

The rate of the acetylation reaction at different concentrations of the inhibitor (and in its absence) was recorded with increasing concentrations of [$^3$H]-acetyl CoA and a constant amount of core histones as well as with increasing concentration of core histones with constant amount of [$^3$H]-acetyl CoA. The double reciprocal plot for each inhibitor concentration and in its absence was plotted. The kinetic results show that the inhibition patterns for p300 and PCAF are similar. When the concentration of acetyl CoA was changed keeping the histone concentration constant, Km increases, while Vmax and Kcat of the reaction decrease. On the other hand increasing concentration of histones with constant amount of [$^3$H]-acetyl CoA increases Km but Vmax and Kcat remain same which indicates that in this context garcinol competes with histones for binding to the active site of the enzyme and thus acts as a competitive inhibitor.

The reaction mechanism for p300 and PCAF to acetylate the lysine residues is contrastingly different. The GNAT (GCN5-related N-acetyltransferase) family members, PCAF and serotonin N-acetyltransferase and GCN5 employ ternary complex mechanisms that involve the ordered binding and release of substrates and products (39). On the other hand p300/CBP (CREB binding protein) family follow the double displacement (ping-pong) mechanisms (40). The dead end analogue of acetyl-CoA, desulfo-CoA was shown to be a linear competitive inhibitor versus acetyl CoA but it behaves as a linear uncompetitive inhibitor versus peptide substrate. Garcinol mediated inhibition kinetics (for both p300 and PCAF) shows that with changing concentration of acetyl CoA it behaves like an uncompetitive type of inhibitor whereas for core histones as a competitive inhibitor. These differences in the inhibition pattern indicate the mechanistic uniqueness of garcinol.

In order to ensure the enzyme specificity as well as substrate specificity we went on to check the effect of garcinol on histone deacetylase 1 (HDAC1) enzyme. The HDAC assay protocol was followed as described previously (31). Deacetylation of core histones in the presence or absence of the compound, garcinol (10 or 20 μM) shows no difference whatsoever. Addition of the solvent of garcinol, DMSO has no effect on the deacetylation of core histones by the recombinant HDAC1. Therefore we can presume that garcinol is specific to the histone acetyltransferase (HAT) activity. In order to verify this HAT specificity we used the HAT dependent in vitro chromatin transcription assay system as described previously (12). The chromatin template was assembled on pG5-ML-array (12) by employing NAP1-assembly system. The assembled chromatin was characterized by DNA supercoiling and partial micrococal nuclease (MNase) digestion assay. A substantial amount of relaxed DNA was found to be supercoiled upon deposition of nucleosome. Since supercoiling assay does not assure the proper spacing of the histone octamer, partial micrococal digestion was performed wherein we found 4-5 well resolved regularly spaced nucleosomes. The results of these assays suggest that the assembled chromatin is appropriate for the in vitro transcription experiments. To establish the HAT specific nature of garcinol we have tested its effect on transcription from DNA, which is not HAT dependent. The chimeric transcriptional activator, Gal4-VP16 activates transcription around 10 fold as compared to basal transcription without any activator. Addition of solvent, Dimethyl sulphoxide (DMSO) or 20 μM and 50 μM garcinol shows no effect on the activator dependent transcription. The activator independent transcription from ML200 promoter was used as a loading control. As reported previously transcription from the chromatin template shows complete dependence on acetylation (absolute requirement of acetyl CoA). Addition of DMSO, marginally represses the transcription. Interestingly, increasing concentration of garcinol (especially 50 μM) represses the HAT dependent chromatin transcription drastically. These data show that garcinol specifically inhibits the HAT activity dependent chromatin transcription but not the transcription from the DNA template.

We have shown that garcinol is a potent inhibitor of HATs both in vitro and in vivo. Furthermore, it also inhibits the HAT dependent transcription from chromatin template. In order to further understand its effect in vivo, we treated the HeLa cells with increasing concentrations of garcinol and performed the apoptosis assay. Effect of garcinol on chromatin fragmentation was investigated for this purpose. HeLa cells treated with hydrogen peroxide to induce the apoptosis were taken as a positive control to test garcinol mediated apoptosis. Fragmented chromatin was analyzed on 1.8% agarose gel. The cells treated with buffer or the solvent (DMSO) did not show any obvious differences, but treatment with hydrogen peroxide yielded huge amount of faster moving species of DNA fragments Same as of hydrogen peroxide treatment, increasing concentration of garcinol (30, 70, and 100 μM) also induces apoptosis and generates smaller DNA fragments. To visualize the chromatin fragmentation in situ, compound treated nuclei were stained with Hoechst (which stains the DNA). In agreement with the DNA fragmentation data hoechst staining of the nuclei also shows that treatment with 50 and 100 μM garcinol induces the fragmentation of nuclei, as indicated by arrows Taken together these data show that histone acetyltransferase inhibitor garcinol stimulates the apoptosis in HeLa cells.

The histone acetyltransferase specificity, induction of apoptosis and more significantly the ability of garcinol to inhibit the histone acetylation in vivo promoted us to investigate its effect on global gene regulation. HeLa cells were treated with 100 μM garcinol for 24 hours and subjected to microarray analysis to investigate its effect on global gene regulation. Genome wide analysis of gene expression using microarrays indicates that treatment of HeLa cells with garcinol causes the down regulation of a larger number of genes (1631 genes) as compared to up regulation (630 genes). Out of 2261 differentially regulated genes, 1445 genes have been annotated and 816 genes are either ETS's or are unknown genes. We sorted out the annotated genes based on the chromosomal localization and represented as a bar graph with differentially regulated genes shown per chromosome. It is evident that on most chromosomes the number of down regulated genes is higher except on Chromosome Y, where there were no down-regulated genes. When normalized for the total number of genes known per chromosome, it turns out that approximately 6-8% of the known genes in almost all the chromosomes are found to be differentially regulated on treatment with garcinol.

We classified the differentially regulated genes in various functional categories based on the available annotation in the public databases and that supplied by the slide manufacturer. Amongst the up-regulated genes are those for Caspase 4 and CED6, which are pro-apoptotic while anti-apoptotic genes like the BCL2 family members and the Fas inhibitory molecule are amongst the down-regulated genes. The ubiquitin conjugating enzyme and the E3 ubiquitin ligase are up regulated, which supports the observed death of treated cells by apoptosis. It was also found that the genes for p53-induced protein PIGPC1 (alternative name for PERP-TP53 apoptosis effector protein) and p21 (CDKN1A-cyclin-dependent kinase inhibitor)-activated kinase 6 which are down-regulated probably because they are targets of p53 and p21 respectively which in turn are regulated by the p300/PCAF histone acetyltransferases. Proto-oncogenes form a class of genes of which more are down regulated than up regulated by this treatment, which emphasizes the role of garcinol as a molecule with anti-cancer activity. Large number of differentially regulated genes involved in metabolism and those categorized as transcription factors or signal transducers has not been included in the table due to space constraints. The exact significance of the result is yet to be determined. A large number of un-annotated genes, which may have a significant role in cellular functioning, are found to be differentially regulated.

Here we show for the first time that garcinol, a polyisoprenylated benzophenone from *Garcinia indica* fruit rind is a small molecule, HAT inhibitor, that can be taken in by the cells.

We have demonstrated that garcinol not only inhibits the histone acetylation by p300 and PCAF in vitro, it also represses the acetylation in vivo in HeLa cells. In correlation with this observation and earlier report (42), garcinol induce apoptosis of HeLa cells in a concentration dependent manner. Garcinol is known to possess antioxidant and anticancer chemopreventive activity (42, 43 and references therein). Recently it has been shown that garcinol induce apoptosis in human leukemia cell lines (44). The present funding of garcinol as an inhibitor of histone acetyltransferases may help to understand the mechanism of garcinol induced apoptosis further.

Presumably, hypoacetylation of histone is a prerequisite of apoptosis. Though the relationship between acetylation of histones and activation of gene expression is not as direct as it was believed to be, overall acetylation is a diagnostic feature of active gene. Thus inhibition of acetylation in vivo would repress majority of the genes. Our microarray analysis of garcinol treated HeLa cell gene expression indeed showed that more than 72% genes (tested) were down regulated. The microarray data further revealed that several proto-oncogenes are down regulated in presence of garcinol, suggesting that garcinol may function as an anticancer compound. However, a systematic investigation using normal (untransformed) and different cancerous cell lines are essential to elucidate the specific role of garcinol for cancer prevention. Since alteration of histone acetylation also has casual relation with the manifestation of other diseases, namely asthma (45) and AIDS, garcinol or its derivatives may serve as lead compounds to design therapeutics for other diseases apart from cancer.

EXAMPLE 9.0

A Process of Preparing Garcinol

Production of Garcinol from *Garcinia Indica* Fruit Rind:

*G. indica* dried fruit (Kokum) rind was extracted with ethanol, and the extract was fractionated by ODS (octadecyl silica) column chromatography eluted stepwise with 60-80% aqueous ethanol. The fractions containing garcinol were concentrated and dried in vacuum. The residue was dissolved in hexane, and the solution was cooled at 5° C. for 2 days. Yellow amorphous precipitate was collected from the solution and washed with cold hexane and recrystallized at room temperature.

Garcinol isolated from the *garcinia indica* fruit with 10-15% yield.

Chemical Synthesis of Garcinol and Derivatives

No literature is available so far for the chemical synthesis of garcinol. Garcinol has a complicated chemical structure, bridged cyclic ring, many isoprene groups and lot of stereochemistry. Therefore, it is very difficult to synthesize garcinol by chemical method.

Compounds of structural formula I and formula II as in FIG. 1.0 where in $R_1$ is OH, halogens, O-Methoxy; O-Ethoxy, O-Isopropoxy, O-Allyoxy, O-Butoxy, O-t-Butoxy, O-Pentoxy, O-Hexyloxy, O—$CH_2$—COOH, O—CO—$CH_2$—Cl, O—$SO_2$—$CH_3$, O—$CH_2$—CHOH—$CH_3$ $R_2$ is OH, halogens, O-Methoxy, O-Ethoxy, O-Isopropoxy, O-Allyoxy, O-Butoxy, O-t-Butoxy, O-Pentoxy, O-Hexyloxy, O—$CH_2$—COOH, O—CO—$CH_2$—Cl, O—$SO_2$—$CH_3$, O—$CH_2$—CHOH—$CH_3$ $R_3$ is OH, halogens, O-Methoxy, O-Ethoxy, O-Isopropoxy, O-Allyoxy, O-Butoxy, O-t-Butoxy, O-Pentoxy, O-Hexyloxy, O—$CH_2$—COOH, O—CO—$CH_2$—Cl, O—$SO_2$—$CH_3$, O—$CH_2$—CHOH—$CH_3$ $R_4$ is OH, halogens, O-Methoxy, O-Ethoxy, O-Isopropoxy, O-Allyoxy, O-Butoxy, O-t-Butoxy, O-Pentoxy, O-Hexyloxy, O—$CH_2$—COOH, O—CO—$CH_2$—Cl, O—$SO_2$—$CH_3$, O—$CH_2$—CHOH—$CH_3$ $R_5$ is OH, halogens, O-Methoxy, O-Ethoxy, O-Isopropoxy, O-Allyoxy, O-Butoxy, O-t-Butoxy, O-Pentoxy, O-Hexyloxy, O—$CH_2$—COOH, O—CO—$CH_2$—Cl, O—$SO_2$—$CH_3$, O—$CH_2$—CHOH—$CH_3$ were prepared by the equimolar reactions of garcinol and isogarcinol with respective halo compounds at 30-40° C. in the presence of alkaline hydroxides or alkaline carbonates, the solvents used were acetone, $CHCl_3$, MDC, EDC etc. The derivatives were purified by column chromatography (octadecyl silica gel) and they were characterized by spectral studies. The derivatives were tested for inhibition of histone acetyl transferase and $IC_{50}$ was in the range of 5-7 µM.

REFERENCES

1. Roth, S. Y., Denu, J. M., and Allis, C. D. (2001) *Ann. Rev. of Biochem.* 70, 81-120.
2. Berger, S. L. (2002) *Curr. Opin genet Dev.* 12, 142-148.
3. Sterner, D. E., and Berger, S. L. (2000) *Microbiol. Mol. Biol. Rev.* 64, 435-459.
4. Marks, P. A., Rifkind, R. A., Richon, V. M., Breslow, R., Miller, T., and Kelly, W. K. (2001) *Nat Rev Cancer.* 1, 194-202.
5. Shikama, N., Lyon, J., and La Thangue, N. B. (1997) *Trends Cell Biol.* 7, 230-236.
6. Wolffe, A. P. (2001) *Oncogene.* 20, 2988-2990.
7. Rouaux, C., Jokic, N., Mbebi Boutiller, S., Leoffler, J. P., and Boutiller, A. L. (2003) *EMBO J.* 22, 6537-6549.
8. Puri, P. L., Sartorelli, V., Yang, X. J., Hamamori, Y., Ogryzko, V., Howard, B. H., Kedes, L., Wang, J. Y., Graessmann, A., Nakatani, Y., and Levrero, M. (1997) *Mol Cell.* 1, 35-45.
9. Spacer, T. E., Jenster, G., Burcin, M. M., Allis, C. D., Zhou, J., Mizzen, C. A., McKenna, N. J., Onate, S. A., Tsai, M. J., and O'Malley, B. W. (1997) *Nature.* 389, 194-198.
10. Hung, H. L., Lau, J., Kim, A. Y., Weiss, M. J., and Blobel, G. A. (1999) *Mol. Cell. Biol.* 19, 3496-3505.
11. Chen, H., Lin, R. J., Xie, W., Wilpitz, D., and Evans, R. M. (1999) *Cell.* 98, 675-686.
12. Kundu, T. K., Palhan, V., Wang, Z., An, W., Cole, P. A., and Roeder, R. G. (2000) *Mol Cell.* 6, 551-561.
13. An, W., Palhan, V. B., Karymov, M. A., Leuba, S. H., and Roeder, R. G. (2002) *Mol Cell.* 9, 811-821.
14. Yang, X. L., Ogryzko, V. V., Nishikawa, J., Howard, B. H., and Nakatani, Y. A. (1996) *Nature.* 382, 319-324.
15. Schiltz, R. L., and Nakatani, Y. (2000) *BBA—Reviews on Cancer.* 1470, M37-M53.

16. Yamauchi, T., Yamauchi, J., Kuwata, T., Tamura, T., Yamashita, T., Bae, N., Westphal, H., Ozata, K., and Nakatani, Y. (2000) *Proc Natl Acad Sci USA.* 97, 11303-11306.
17. Ogryzko, V. V., Kotani, T., Zhang, X., Schiltz, R. L., Howard, T., Yang, X. J., Howard, B. H., Qin, J., and Nakatani, Y. (1998) *Cell.* 94, 35-44.
18. Kumar, P. B. R., Swaminathan, V., Banerjee, S., and Kundu, T. K. (2001) *J. Biol. Chem.* 276, 16804-16806.
19. Bonaldi, T., Talamo F., Scaffidi, P., Ferrera, D., Porta, A., Bachi, A., Rubartelli, A., Agresti, A., and Bianchi, E. (2003) *EMBO J.* 22, 5551-5560.
20. Kaehlcke, K., Dorr, A., Hetzer-Egger, C., Kiermer, V., Henklein, P., Schnoelzer, M., Loret, E., Cole, P. A., Verdin, E., and Ott, M. (2003) *Mol Cell.* 12, 167-176.
21. Bres, V., Tagami, H., Peloponese, J. M., Loret, E., Jeang, K. T., Nakatani, Y., Emiliani, S., Benkirane, M., and Kieman, R. E. (2002) *EMBO J.* 21, 6811-6819.
22. Borrow, J., Stanton, V P. Jr., Andresen, J. M., Becher, R., Behm, F. G., Chaganti, R. S., Civin, C. I., Disteche, C., Dube, I., Frischauf, A. M., Horsman, D., Mitelman, F., Volinia, S., Watmore, A. E., and Housman, D. E. (1996) *Nat Genet.* 14, 3341.
23. Murata, T., Kurokawa, R., Krones, A., Tatsumi, K., Ishii, M., Taki, T., Masuno, M., Ohashi, H., Yanagisawa, M., Rosenfeld, M. G., Glass, C. K., and Hayashi, Y. (2001) *Hum Mol Genet.* 10, 1071-1076.
24. Kalkhoven, E., Roelfsema, J. H., Teunissen, H., Den Boer, A., Ariyurek, Y., Zantema, A., Breuning, M. H., Hennekam, R. C., and Peters, D. J. (2003) *Hum. Mol. Genet.* 12, 441-450.
25. Lusic, M., Marcello, A., Cereseto, A., and Giacca, M. (2003) *EMBO J.* 22, 6550-6561.
26. Quivy, V., Adam, E., Collette, Y., Demonte, D., Chariot, A., Vanhulle, C., Berkhout, B., Castellano, R., De Launoit, Y., Burny, A., Piette, J., Bours, V., and Van Lint, C. (2002) *J. Virol.* 76, 11091-11103.
27. Richon, V. M., Zhou, X., Rifkind, R. A., and Marks, P. A. (2001) *Blood Cells Mol Dis.* 27, 260-264.
28. Cullis, P. M., Wolfenden, R., Cousens, L. S., and Alberts, B. M. (1982) *J. Biol. Chem.* 257, 12165-12169.
29. Lau, O. D., Kundu, T. K., Soccio, R. E., Ait-Si-Ali, S., Khalil, E. M., Vassilev, A., Wolfee, A. P., Nakatani, Y., Roeder, R. G., and Cole, P. A. (2000) *Mol Cell.* 5, 589-595.
30. Cebrat, M., Kim, C. M., Thompson, P. R., Daugherty, M., and Cole, P. A. (2003) *Bioorg. Med. Chem.* 11, 3307-3313.
31. Balasubramanyam, K., Swaminathan, V., Ranganathan, A., and Kundu, T. K. (2003). *J. Biol. Chem* 278, 19134-19140.
32. Kundu, T. K., Wang, Z., and Roeder, R. G. (1999) *Mol. Cell. Biol.* 19, 1605-1615.
33. Wen-Ling Shaiu and Tao-Shis Hsieh. (1998) *Mol. Cell Biol.* 18, 4358-4367
34. Chambers, A. E., Banerjee, S., Chaplin, T., Dunne, J., Debernardi, S., Joel, S. P., and Young, B. D. (2003) *Eur. J. Cancer.* 39, 1165-1175.
35. Ryan, C. A., and Annunziato, A. T. (2001) *Current Protocols in Molecular Biology* (Canada V., ed.) John Wiley and Sons Inc., New York, Chapter 21; Unit 2.2, pp. 2.3-2.10.
36. Bonner, W. M., West, M. H., and Stedman, J. D. (1980) *Eur. J Biochem.* 109, 17-23.
37. Pillai, B., Brahmachari, S. K., and Sadhale, P. P. (2001) *Curr. Sci.* 81, 574-578.
38. Wolffe, A. (1998) Chromatin structure and function. *Academic Press*, Third edition page 97-105.
39. Tanner, K. G., Langer, M. R., and Denu, J. M. (2000) *Biochemistry.* 39, 11961-11969.
40. Thompson, P. R., Kurooka, H., Nakatani, Y., and Cole, P. A. (2001) *J. Biol. Chem.* 276, 33721-33729.
41. Polesskaya, A., Naguibneva, I., Fritsch, L., Duquet, A., Ait-Si-Ali, S., Robin, P., Vervisch, A., Pritchard, L. L., Cole, P. A., and Harel-Bellan, A. (2001) *EMBO J.* 20, 6816-6825.
42. Pan, M. H., Chan, W. L., Lin-Shiau, S. Y., and Lin, J. K. (2001) *J. Agri. Food Chem.* 49, 1464-1474.
43. Ito, C., Itoigawa, M., Miyamoto, Y., Onoda, S., Rao, K. S., Mukainaka, T., Tokuda, H., Nishino, H., and Farukawa, H. (2003) *J Nat Prod.* 66, 206-209.
44. Matsumoto, K., Akao, Y., Kobayashi, E., Ito, T., Ohguchi, K., Tanaka, T., Linuma, M., and Nozawa, Y. (2003) *Biol Pharm Bull.* 26, 569-571.
45. Kagoshima, M., Ito, K., Cosio, B., and Adcock, I. M. (2003) *Biochem Soc Trans.* 31, 61-65.
46. Yamaguchi, F., Saito, M., Ariga, T., Yoshimura, Y., and Nakazawa H. (2000) *J Agric Food Chem.* 48, 2320-2325

We claim:

1. Derivatives of compounds Garcinol and Isogarcinol of

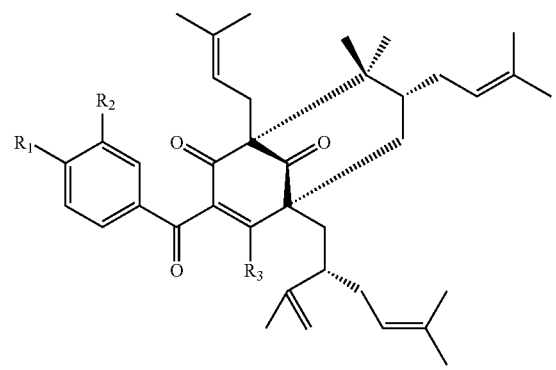

FORMULA I

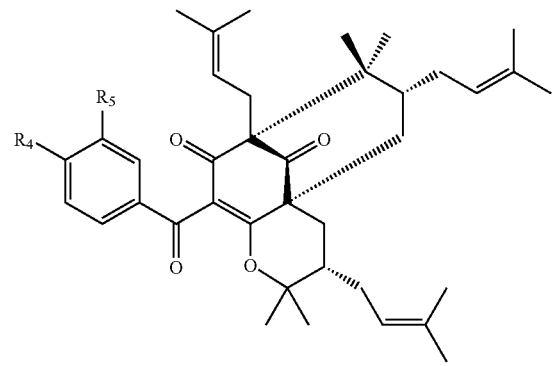

FORMULA II respectively, wherein R1, R2 and R3, substituents of Garcinol, and R4 and R5, substituents of Isogarcinol, are selected from a group consisting of Methoxy, Ethoxy, Isopropoxy, Allyloxy, Butoxy, t-Butoxy, Pentoxy, Hexyloxy, O—CH2—COOH, O—CO—CH2Cl, O—SO2—CH3, and O—CH2—CHOH—CH3.

2. A process for preparation of derivatives of compound Garcinol and Isogarcinol of formula I and II, respectively, said process comprising steps of reacting Garcinol or Isogarcinol with halo compounds to obtain the derivatives with the selected substituents of R1, R2, R3, R4 and R5, at temperature ranging between 30-40° C. under alkaline conditions in presence of organic solvents, and purifying the derivatives.

3. The process as claimed in claim 2, wherein the reacting process is carried in presence of at least one of alkaline hydroxides or alkaline carbonates.

4. The process as claimed in claim 2, wherein the compounds Garcinol and Isogarcinol are in equimolar concentration.

5. The process as claimed in claim 2, wherein the organic solvent is selected from a group consisting of acetone, chloroform, MDC and EDC.

6. The process as claimed in claim 2, wherein the purifying process of the derivatives is conducted by column chromatograpy.

7. A method of inhibiting histone acetyltransferase (HAT) in a subject, wherein said method comprises a step of administering a derivative of Garcinol or Isogarcinol of formula I or formula II

FORMULA I

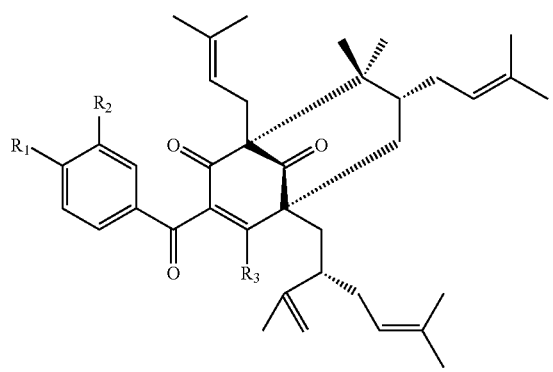

-continued

FORMULA II respectively, to the subject, wherein R1, R2, and R3, substituents of the Garcinol derivative of formula I, and R4 and R5, substituents of the Isogarcinol derivative of formula II, are selected from the group consisting of methoxy, ethoxy, isopropoxy, allyloxy, butoxy, t-butoxy, pentoxy, hexyloxy, O—CH2—COOh, O—CO—CH2Cl, O—SO2—CH3, and O—CH2—CHOH—CH3.

8. The method as claimed in claim 7, wherein the derivatives are HAT inhibitors.

9. The process as claimed in claim 2, wherein said halo compounds are selected from a group consisting of halogens and HOCO—$CH_2$—Cl.

10. The method as claimed in claim 7, wherein the subject suffers from at least one disease selected from the group consisting of cancer, asthma, cardiac hypertrophy, and acquired immunodeficiency syndrome.

* * * * *